United States Patent
Porthiyas et al.

(10) Patent No.: US 11,628,096 B2
(45) Date of Patent: Apr. 18, 2023

(54) SENSING DEVICE AND CHARGING SYSTEM

(71) Applicant: ESSITY HYGIENE AND HEALTH AKTIEBOLAG, Gothenburg (SE)

(72) Inventors: Danny Porthiyas, Toronto (CA); Shyam Mali, Toronto (CA); Jacob Edding, Mississauga (CA); Stopher Christensen, Mississauga (CA); Timothy Ahong, Toronto (CA); Joel Ironstone, Toronto (CA); Jeremy Dabor, Brantford (CA); Catherine Sauve, Edmonton (CA); Sameer Dhar, Edmonton (CA)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 0 days.

(21) Appl. No.: 16/335,705

(22) PCT Filed: Jul. 4, 2017

(86) PCT No.: PCT/EP2017/066607
§ 371 (c)(1),
(2) Date: Mar. 22, 2019

(87) PCT Pub. No.: WO2018/015141
PCT Pub. Date: Jan. 25, 2018

(65) Prior Publication Data
US 2019/0247241 A1    Aug. 15, 2019

Related U.S. Application Data

(60) Provisional application No. 62/365,423, filed on Jul. 22, 2016.

(51) Int. Cl.
| A61F 13/42 | (2006.01) |
| H02J 7/00 | (2006.01) |
| A61F 13/84 | (2006.01) |

(52) U.S. Cl.
CPC .......... *A61F 13/42* (2013.01); *H02J 7/0044* (2013.01); *A61F 2013/424* (2013.01);
(Continued)

(58) Field of Classification Search
None
See application file for complete search history.

(56) References Cited

U.S. PATENT DOCUMENTS 4,834,733 A * 5/1989 Huntoon ................. A61F 13/42
604/361
5,036,859 A * 8/1991 Brown ....................... A61F 5/48
340/573.5

(Continued)

FOREIGN PATENT DOCUMENTS

| CN | 101854895 A | 10/2010 |
| CN | 201631499 U | 11/2010 |

(Continued)

OTHER PUBLICATIONS

Examination report No. 1 issued in Australian patent application No. 2017298352, dated Mar. 31, 2020.
(Continued)

*Primary Examiner* — Fekadeselassie Girma
(74) *Attorney, Agent, or Firm* — Cantor Colburn LLP (57) ABSTRACT

This disclosure relates to a combination of a sensing device and a charging system. The sensing device is configured to be applied to a surface of an absorbent article for sensing a characteristic of moisture in the absorbent article, and it is configured such that a transmitter for transmitting data from the sensing device is attached or attachable to the sensing
(Continued)

device. The charging system is configured to charge a transmitter battery, and it is configured such that a transmitter, which is attached or attachable to the sensing device, is also attachable to the charging device.

27 Claims, 4 Drawing Sheets

(52) U.S. Cl.
CPC ............... *A61F 2013/8482* (2013.01); *A61F 2013/8497* (2013.01); *H02J 7/0049* (2020.01)

(56) References Cited

U.S. PATENT DOCUMENTS

| | | | | |
|---|---|---|---|---|
| 5,258,745 A * | 11/1993 | Colling | | A61F 5/48 340/573.5 |
| 5,264,830 A * | 11/1993 | Kline | | A61F 13/42 340/573.5 |
| 5,416,469 A * | 5/1995 | Colling | | A61F 5/48 340/573.5 |
| 5,838,240 A * | 11/1998 | Johnson | | A61F 5/48 604/361 |
| 6,246,330 B1 * | 6/2001 | Nielsen | | A61F 13/42 340/384.1 |
| 6,448,464 B1 * | 9/2002 | Akin | | A61F 13/15203 604/378 |
| 6,479,727 B1 * | 11/2002 | Roe | | A61F 13/42 604/362 |
| 8,207,394 B2 * | 6/2012 | Feldkamp | | A61F 13/42 604/362 |
| 8,866,624 B2 * | 10/2014 | Ales, III | | A61F 13/42 340/532 |
| 9,645,218 B2 * | 5/2017 | Schroers | | A61M 1/3653 |
| 9,726,629 B2 * | 8/2017 | Bhatia | | G01N 27/07 |
| 10,130,523 B2 * | 11/2018 | Geloen | | A61F 13/42 |
| 10,350,115 B2 * | 7/2019 | Long | | A61F 13/42 |
| 10,356,138 B2 * | 7/2019 | Novo Diaz | | H04L 41/12 |
| 2002/0090981 A1 * | 7/2002 | Bae | | H04R 1/1033 455/575.5 |
| 2002/0155821 A1 * | 10/2002 | Louis | | H03F 1/3229 455/126 |
| 2004/0207530 A1 * | 10/2004 | Nielsen | | A61F 13/42 340/573.5 |
| 2004/0220538 A1 * | 11/2004 | Panopoulos | | A61F 13/42 604/361 |
| 2005/0033250 A1 * | 2/2005 | Collette | | A61F 13/42 604/361 |
| 2005/0156744 A1 * | 7/2005 | Pires | | A61F 13/42 340/573.5 |
| 2005/0195085 A1 * | 9/2005 | Cretu-Petra | | A61F 13/42 340/573.5 |
| 2005/0245839 A1 * | 11/2005 | Stivoric | | A61B 10/0012 374/E1.004 |
| 2007/0013533 A1 * | 1/2007 | Zazzara | | A61F 13/42 340/604 |
| 2007/0046482 A1 * | 3/2007 | Chan | | A61F 13/42 340/604 |
| 2007/0100666 A1 * | 5/2007 | Stivoric | | A63F 13/211 374/E1.002 |
| 2007/0260209 A1 * | 11/2007 | Brilman | | A61B 5/6804 116/109 |
| 2008/0021428 A1 * | 1/2008 | Klofta | | A61F 13/42 604/385.01 |
| 2008/0094226 A1 * | 4/2008 | O'Shea | | A61B 5/6804 340/572.1 |
| 2008/0297325 A1 * | 12/2008 | Torstensson | | A61B 5/00 340/10.42 |
| 2009/0056139 A1 * | 3/2009 | Royle | | B26B 19/3806 30/526 |
| 2009/0326417 A1 * | 12/2009 | Ales, III | | G16H 40/63 600/584 |
| 2010/0168694 A1 * | 7/2010 | Gakhar | | G01N 21/3554 604/361 |
| 2010/0241094 A1 * | 9/2010 | Sherron | | A61F 13/42 604/361 |
| 2010/0283617 A1 * | 11/2010 | Huang | | A61F 13/42 340/573.5 |
| 2010/0328075 A1 * | 12/2010 | Rahamim | | A61F 5/56 340/573.1 |
| 2011/0095884 A1 * | 4/2011 | Xu | | A61F 13/42 340/539.11 |
| 2011/0137274 A1 * | 6/2011 | Klofta | | A61L 15/56 604/361 |
| 2011/0245732 A1 * | 10/2011 | Mravyan | | A61B 5/1116 600/587 |
| 2012/0053424 A1 * | 3/2012 | Kenalty | | A61B 5/0205 600/300 |
| 2012/0256750 A1 * | 10/2012 | Novak | | A61F 13/42 340/573.5 |
| 2012/0299730 A1 * | 11/2012 | Rahimi | | G08B 21/0288 600/595 |
| 2013/0165809 A1 * | 6/2013 | Abir | | A61B 5/113 600/534 |
| 2014/0059837 A1 * | 3/2014 | Schroers | | A61B 5/443 324/601 |
| 2014/0262774 A1 * | 9/2014 | Bhatia | | G01N 27/07 204/403.01 |
| 2014/0266723 A1 | 9/2014 | Grant et al. | | |
| 2014/0266734 A1 * | 9/2014 | Chen | | A61F 13/42 340/573.5 |
| 2014/0375297 A1 * | 12/2014 | Geiger | | A61F 13/42 604/361 |
| 2015/0042489 A1 * | 2/2015 | LaVon | | A61F 13/49 340/870.11 |
| 2015/0077261 A1 * | 3/2015 | Lineberry | | A61F 13/42 340/604 |
| 2015/0080819 A1 * | 3/2015 | Charna | | A61F 13/42 604/361 |
| 2015/0150732 A1 * | 6/2015 | Abir | | A61F 13/42 356/445 |
| 2015/0157512 A1 * | 6/2015 | Abir | | A61B 5/08 340/573.5 |
| 2015/0164703 A1 * | 6/2015 | Bae | | A61F 13/42 324/693 |
| 2015/0223755 A1 * | 8/2015 | Abir | | A61B 90/30 600/300 |
| 2015/0267176 A1 * | 9/2015 | Joung | | C12N 9/22 435/375 |
| 2016/0120455 A1 * | 5/2016 | Pop | | A61F 13/42 600/301 |
| 2016/0149394 A1 * | 5/2016 | Trusty | | H02H 5/00 361/59 |
| 2016/0307430 A1 * | 10/2016 | Chen | | G08B 21/20 |
| 2017/0258643 A1 * | 9/2017 | Xu | | A61F 13/42 |
| 2018/0325743 A1 * | 11/2018 | Ho | | A61F 13/42 |
| 2019/0167488 A1 * | 6/2019 | Sobti | | A61F 13/42 |
| 2019/0224051 A1 * | 7/2019 | Kutay | | A61F 13/42 |
| 2019/0362147 A1 * | 11/2019 | Adam | | G06V 20/188 |
| 2019/0392830 A1 * | 12/2019 | Abdollahian | | G06V 10/764 |
| 2020/0065054 A1 * | 2/2020 | Fink | | G06F 3/165 |
| 2020/0066022 A1 * | 2/2020 | Leong | | G06F 3/0482 |
| 2020/0137509 A1 * | 4/2020 | Stanek | | H04S 7/303 |
| 2020/0196035 A1 * | 6/2020 | Rousseaux | | H04J 14/0206 |
| 2020/0268125 A1 * | 8/2020 | Apte | | A45D 29/00 |

FOREIGN PATENT DOCUMENTS

| | | | | |
|---|---|---|---|---|
| CN | 102332934 A | * | 1/2012 | |
| CN | 204260921 U | * | 4/2015 | |
| CN | 204744627 U | * | 11/2015 | |
| CN | 105301196 A | * | 2/2016 | ......... G01N 33/0027 |
| CN | 104066409 B | | 11/2016 | |
| DE | 2933991 C2 | * | 11/1989 | ............ H03J 5/0281 |
| DE | 202 04 897 U1 | | 7/2002 | |
| JP | H05180800 A | | 7/1993 | |
| WO | 2006119523 A1 | | 11/2006 | |
| WO | WO-2010012217 A1 | * | 2/2010 | .............. A61F 13/42 |

(56) References Cited

FOREIGN PATENT DOCUMENTS

| WO | WO-2011145787 A1 | * | 11/2011 | ............. | A61F 13/42 |
| WO | 2016090492 A1 | | 6/2016 | | |
| WO | WO-2017146494 A1 | * | 8/2017 | ............. | A61F 13/44 |

OTHER PUBLICATIONS

National Intellectual Property Administration (CNIPA) of the People's Republic of China, Notification of the First Office Action, Application No. 201780056880.6, dated Nov. 12, 2020 (18 pages).
IP Australia, Examination report No. 2 for standard patent application, Application No. 2017298352, dated Oct. 7, 2020 (5 pages).
Australian Government, IP Australia, Examination report No. 3 for standard patent application, Application No. 2017298352, dated Mar. 17, 2021 (5 pages).
European Office Action issued in European patent application No. 17 736 643.2, dated Dec. 12, 2019.
National Intellectual Property Administration (CNIPA) of the People's Republic of China, Notification of the Second Office Action, Application No. 201780056880.6, dated Jul. 5, 2021 (7 pages).
European Patent Office, Communication pursuant to Article 94(3) EPC, Application No. 17 736 643.2, dated Apr. 23, 2021 (5 pages).
European Patent Office, Communication pursuant to Article 94(3) EPC, Application No. 17 736 643.2, dated Sep. 9, 2021 (4 pages).
National Intellectual Property Administration (CNIPA) of the People's Republic of China, Notification of the Third Office Action, Application No. 201780056880.6, dated Oct. 21, 2021 (11 pages).
Decision of Rejection issued in Chinese Patent Application No. 201780056880.6; Application Filing Date Jul. 4, 2017; dated Jan. 30, 2022 (13 pages).
Decision to Grant issued in European Patent Application No. 17736643.2; Application Filing Date Jul. 4, 2017; dated Jun. 7, 2022 (7 pages).

* cited by examiner

SENSING DEVICE AND CHARGING SYSTEM

CROSS-REFERENCE TO PRIOR APPLICATION

This application is a § 371 National Stage Application of PCT International Application No. PCT/EP2017/066607 filed on Jul. 4, 2017, which claims priority to U.S. Provisional Application No. 62/365,423 filed on Jul. 22, 2016, both of which are incorporated herein in their entirety.

TECHNICAL FIELD

The present disclosure relates to a combination of a sensing device, configured to sense moisture in absorbent articles, and of a charging system configured to charge a transmitter battery of a transmitter for transmitting data from the sensing device. The present disclosure further relates to a sensing device and to a charging system as stand-alone components.

TECHNICAL BACKGROUND

Sensing devices, such as a removable sensor strips for being removably fixed to an absorbent article, may be used to sense moisture in absorbent articles such as diapers, incontinence garments, dressings, or pads. The sensing device is provided with at least one sensor for detecting wetness events (e.g., caused by incontinence).

The removable sensing device may be temporarily applied to an absorbent article, detect wetness events, and may then, after use, be removed from the absorbent article. The absorbent article and the sensing device may be separately disposed, thus allowing for an environment-friendly waste separation. The use of absorbent articles with a removable sensor strip offers the further advantage over using an absorbent article with an integrated sensor that a user may decide to selectively use (or not use) the sensor strip. For example, a user may use diapers without a sensor strip during the day but switch to the use of a sensing strip for the night.

However, the use of sensing devices generates additional costs for absorbent articles users. In particular, a sensing device contains electronic components such as one or several sensor(s). Some sensing devices also include a transmitter configured to transmit data about whether a wetness event has occurred to a corresponding receiver. The use of such a transmitter allows a user to see whether the event has taken place from the outside, even when the absorbent article is covered by clothes, etc. In addition, disposing large quantities of sensing devices including electronic components also generates a considerable amount of undesirable waste.

Hence, it is desired for a sensing device for sensing moisture in an absorbent article, and, possibly, for other components configured to work together with the sensing device, which address at least one of the above mentioned shortcomings.

SUMMARY

One aspect of the present disclosure meeting some of the above mentioned shortcomings relates to a combination of a sensing device and a charging system. The combination may be a kit of parts and/or an assembly in the sense that the sensing device and the charging system are specifically adapted to one another. In other words, the sensing device and the charging system do not have independent configurations but are configured to work together, analogous to the configuration for working together of a key and a keyhole. However, the disclosure also encompasses embodiments of a sensing device and embodiments of a charging system which are designed independently from any counterpart.

The combination may include one or several further components in addition to the sensing device and the charging system. In a particular embodiment, the combination consists of the sensing device and the charging system. The sensing device, as a part of the combination, is configured to be applied to a surface of an absorbent article for sensing a characteristic of moisture in the absorbent article. In a particular embodiment, it is configured to be applied to an outer/exterior surface. For example, it may be configured to be stripped to a diaper, worn by a user, at an outer/exterior diaper surface. In particular embodiments, the sensing device is configured to sense a characteristic of moisture in an absorbent article without being in direct contact with fluid/liquid/moisture. The characteristic of moisture may include a presence of moisture and/or an amount of moisture present in an absorbent article.

The sensing device, as a part of the combination in accordance with the present disclosure, is configured such that a transmitter for transmitting data from the sensing device (to a corresponding receiver) is attached or attachable to the sensing device. A transmitter may be fixedly or removably attached to the sensing device. Some embodiments of the combination in accordance with the present disclosure include a transmitter which is specifically designed to work together with the sensing device in the sense that the transmitter is adapted specifically so as to be suitable to be attached (to be "attachable") to the sensing device.

The charging system, as a part of the combination in accordance with the present disclosure, is configured to charge a transmitter battery, the charging system further being configured such that a transmitter, which is attached or attachable to the sensing device, is also attachable to the charging device. In other words, the sensing device and the charging system are "compatible" (i.e., they are configured to work together) in the sense that the same transmitter which is attached or attachable to the sensing device is also attachable to the charging system.

One of the advantages of the combination in accordance with the present disclosure is that the sensing device is (preferably often) reusable in a convenient manner. It is possible to recharge the battery of a transmitter included in or used with the sensing device. This may mean that at least transmitters need to be replaced less often. This may lead to a reduction of waste, may therefore be environment-friendly, while it may even lower the costs for users. Further, especially in the case of embodiments wherein the transmitter is removably attachable to the sensing device, a sensing device without the transmitter may be disposed and replaced, and then the same transmitter may be used with the next sensing device. In this way, a selective increase of the lifespan of particular components is made possible, thus selectively lowering waste and increasing the replacement interval of a (relatively) costly component such as a transmitter.

Components wherein the disadvantage of increased manufacturing costs and/or the increased inconvenience during use associated with providing this/these component(s) separately/removably outweighs the benefit of lowering waste and costs for the user, may be fixedly integrated in the sensing device. For example, the sensing device may be formed with a built-in sensor. In contrast, components wherein the disadvantage of increased manufacturing costs and/or the increased inconvenience during use associated with providing them separately/removably is outweighed by the benefit of lowering waste and costs for the user (such as in the case of a transmitter), may be provided as a separate component.

In some embodiments, the sensing device includes a first attachment member for attaching a transmitter to the sensing device. In some embodiments, the charging system includes a second attachment member for attaching a transmitter to the charging system. The labels "first" and "second" are merely used as labels to distinguish between the attachment members but either of them can be present on its own in the case of some embodiments of the combination in accordance with the present disclosure.

According to some embodiments, the first attachment member includes a fastener, a conductive and/or a non-conductive adhesive, a releasable snap-fit connection mechanism, a magnet, a rivet, a staple, epoxy, and/or a latch mechanism. Any suitable means for (if applicable: releasably) attaching a transmitter to the first attachment member may be applied. Similarly, according to some embodiments, the second attachment member includes a fastener, a conductive and/or a non-conductive adhesive, a releasable snap-fit connection mechanism, a magnet, and/or a latch mechanism. Any suitable means for (if applicable: releaseably) attaching a transmitter to the second attachment member may be applied.

According to some embodiments, the combination includes a sensing system, said sensing system including the sensing device and a transmitter. The transmitter can be a wireless transmitter.

In some embodiments, the transmitter is attached or attachable to the first attachment member and attachable to the second attachment member. In other words, the transmitter may be fixedly attached to the first attachment member of the sensing device or it may be separable. In the first case, the entire sensing device together with the fixedly attached transmitter may be (removably) attached to the second attachment member of the charging system to charge the battery of the transmitter. In the second case, the transmitter may be detached from the first attachment member of the sensing device and may be then attached, as a separate entity, to the second attachment member of the charging system for being charged. In some embodiments, the user may have the choice of either detaching or not detaching the transmitter from the sensing device and either charging the transmitter battery with the whole sensing system attached to the charging system or with only the transmitter being separately attached. In other embodiments, the user must detach the transmitter from the charging system before attaching it to the charging system and charging the transmitter battery.

According to some embodiments, the first attachment member and the transmitter include mating electrical connections such as conductive pads. Alternatively or additionally thereto, the second attachment member and the transmitter of some embodiments include mating electrical connections such as conductive pads.

In particular embodiments, it is desired for the transmitter to be detachable from the first attachment member and/or from the second attachment member. This increases user convenience. If the transmitter is detachable from the first attachment member, a sensing device may be disposed while the user may go on using the transmitter with another sensing device.

The sensing device of a combination in accordance with the present disclosure also can be configured to sense movements, a location, and/or a position of a wearer of an absorbent article to which the sensing device has been applied.

Another aspect of the disclosure relates to a sensing device for the combination according to any one of the aforementioned aspects/embodiments. This sensing device is a stand-alone component. The sensing device, as a stand-alone component, suitable for use as a part of a combination according to the present disclosure, may have any of the features associated with a sensing device as a part of a combination as described in this disclosure. Likewise, a sensing device as a part of a combination in accordance with this disclosure may have any of the features of a sensing device as a stand-alone component.

In some embodiments, the sensing device comprises or consists of a sensor strip, for example a disposable sensor strip. The sensing device may include metal, plastic, and/or paper. The sensor strip may be stripped to a diaper from the outside and may be configured to sense a wetness event without being in contact with a zone of the diaper which is wet. In other words, it may sense the wetness event merely by being in contact with an exterior/outer surface of the diaper, for example, by detecting whether an electric or magnetic current/field is interrupted or whether the strength thereof is changed, and/or by detecting a change in electric and/or magnetic resistivity.

According to some embodiments, the sensing device consists of the sensor strip and the first attachment member.

In some embodiments, the sensing device includes a substrate and one or more sensors provided on or in the substrate, said substrate including a flex printed circuit board (PCB) covered within a jacket or a coating. In some embodiments, the one of the one or more sensors protrude(s) outwardly away from a surface of the substrate. This is advantageous as the sensor(s) may be pressed against an outer surface of an absorbent article when the sensing device is fastened/attached to the absorbent article for use. A high detection reliability and/or accuracy may hereby be promoted.

The sensor may be configured to measure an impedance of an absorbent article from a location on an exterior surface of the absorbent article. More generally, the sensing device may include an impedance sensing element, wherein the impedance sensing element includes electrode, an attachment member for securing the impedance sensing element at a location on an exterior surface of an absorbent article, wherein the electrodes are positioned so as to be capacitively coupled to an interior region of the absorbent article and to measure an impedance of the absorbent article from the location on the exterior surface of the absorbent article. The sensing device may further include an impedance measurement subsystem for measuring the impedance of the absorbent article, and for extracting a real component of the impedance and an imaginary component of the impedance for determining a characteristic of the moisture in the absorbent article. The impedance measurement subsystem may further be configured to measure an impedance between the electrodes.

The sensor for detecting wetness in an absorbent article may also for instance be a capacitance-based sensor such as described in U.S. Pat. No. 8,866,624, an inductance-based sensor such as described in U.S. Pat. No. 8,207,394, or an infrared reflectance-based sensor, such as described in US 2010/0168694 A1. Any other suitable sensor technology can be employed.

According to some embodiments, the at least one sensor(s) include(s) an electrode provided in a protruding portion of said sensor. This is advantageous as the electrode(s) may be pressed against an outer surface of an absorbent article when the sensing device is fastened/attached to the absorbent article for use. A high detection reliability and/or accuracy is hereby promoted.

According to some embodiments, at least one of the one or more sensors is at least partially formed by one or more conductive elastomers embedded in or deposited on the substrate. The flexibility of elastomers allows the sensing part of the device to conform to the shape of a surface to which the sensing device is applied, thereby promoting a good contact and, hence, a high detection reliability/accuracy.

In some embodiments, the sensing device is configured to be applied to an absorbent article so that a surface of the substrate faces an exterior surface of the absorbent article and that at least one of the one or more sensors presses against the exterior surface of the absorbent article.

Another aspect of this disclosure relates to a sensing system, as a stand-alone component, for the combination according to any one of the aspects/embodiments described in this disclosure. The sensing system may include the sensing device according to any one of the aspects/embodiments described in this disclosure.

Another aspect of this disclosure relates to a charging system, as a stand-alone component, for the combination according to any one of the aspects/embodiments described in this disclosure. The charging system may be specifically designed to work together with any aspect/embodiment of a sensing device and/or sensing system described in this disclosure.

According to some embodiments, the charging system includes a first light source, the charging system being configured to emit light with the first light source for indicating that the charging system is capable of charging a transmitter battery, and/or whether the charging system is connected to power, and/or whether a transmitter is attached, and/or a charging status of a transmitter. This promotes a high user convenience.

In some embodiments, the charging system includes a base, wherein the base includes the second attachment member for attaching a transmitter to the base. The base can include a cavity for accommodating the sensing device (and/or the sensing system comprising the device) according to any one of the aspects/embodiments described in this disclosure. This further increases user convenience regarding the charging system. In particular, a user may, e.g., take the charging system along, with a replacement sensing device neatly tucked away in the charging system's base, when going out (e.g., when taking a baby out shopping or on a trip), and then replace the sensing device when needed.

In addition thereto, or alternatively, the charging system may include a cover with an opening or window allowing light emitted from the first light source to be visible from outside of the charging system when the cover is closed. The charging system (especially the charging part, i.e., the port with electronic components, to which a transmitter is docketed) is further protected from dust and other detrimental outside influences. Nevertheless, optimal visibility for a charging operation may be provided to a user.

The second attachment member and the first light source of some embodiments are positioned such that a transmitter covers the first light source when the transmitter is attached to the second attachment member. This way, it may be conveniently visible whether there is already a transmitter attached to the charging system or not. In addition, focus may also be exclusively drawn to information from a light source on the transmitter (if present) when the transmitter is docketed to the charging system.

Another aspect of this disclosure relates to a charging system configured to charge a transmitter battery of a transmitter for transmitting data from a sensing device, the transmitter being detachably attachable to the charging device. The charging device includes a first light source and is configured to emit light with the first light source for indicating that the charging system is capable of charging a transmitter battery, and/or whether the charging system is connected to power, and/or whether a transmitter is attached, and/or a charging status of a transmitter. This stand-alone charging system which may or may not be specifically designed/adapted to work together with any other component, may have any of the described features of a charging system for a combination as described above, and vice versa.

A combination according to an embodiment, wherein a transmitter is provided and wherein the charging system includes an opening or window as described above, includes a transmitter including a second light source, wherein the opening or window is positioned on the cover such that light emitted from the second light source is visible from outside of the charging system when the transmitter is attached to the second attachment member and the cover is closed. This allows displaying information to a user concerning the charging of a transmitter (battery) in a very and convenient way. For example, the first light source may emit light of a first color, and the second light source may emit light of a second color. The first color may, hence, signal that no transmitter is being charged and that the charging system is "free"/ready for charging. The second color may signal that a transmitter is being charged. Further distinctions can be made, e.g., by virtue of different emission patterns/frequencies, etc. For example, continuous light of the second color may symbolize a charging operation, whereas blinking light may signal that the transmitter is fully charged.

The labels "first" and "second" pertaining to the light sources, are merely used to distinguish between the light sources. However, either the first or the second light source may also be present on their own (i.e., independently from one another).

In some embodiments, the transmitter is configured to emit light with the second light source for indicating a charging status of a battery of the transmitter. The charging status may be "charging" or "fully charged", or it may also indicate to what extent a transmitter is charged ("half charged", 70%, etc.).

Another aspect of this disclosure concerns a sensing device, as a stand-alone component, configured to be applied to a surface of an absorbent article for sensing a characteristic moisture in the absorbent article, the sensing device including a substrate and one or more sensors provided on or in the substrate, wherein at least one of the one or more sensors protrudes outwardly away from a surface of the substrate. The characteristic may, e.g., merely indicate whether moisture is present, and/or the amount of moisture. Reference is made to the further explanations provided above. Further, the sensing device may have any of the features of a sensing device according to any of the aspects/embodiments described earlier on, and vice versa. Reference is thus explicitly made to all of the aspects described for a sensing device (and for a sensing system, etc.) earlier on.

The functional characterization of being suited "for a combination" mentioned in connection with aspects/embodiments of a sensing device, a sensing device, and/or a charging system, is to be read as indicating that the respective device/system is a part of the combination/a part of the respective assembly, kit of parts, in the sense that it is specifically designed to work together with another component of the combination, assembly, kit of parts, i.e., a design for working together analogous to the matching design of a combination of a key and a keyhole.

Additional advantages and features of the present disclosure, that can be realized on their own or in combination with one or several features discussed above, insofar as the features do not contradict each other, will become apparent from the following description of embodiments.

BRIEF DESCRIPTION OF THE DRAWINGS

For a better understanding of the present disclosure and to show how the same may be carried into effect, reference will now be made, by way of example only, to the accompanying drawings, in which.

The description is given with reference to the accompanying drawings, in which.

DETAILED DESCRIPTION OF PARTICULAR EMBODIMENTS

Figure 1:
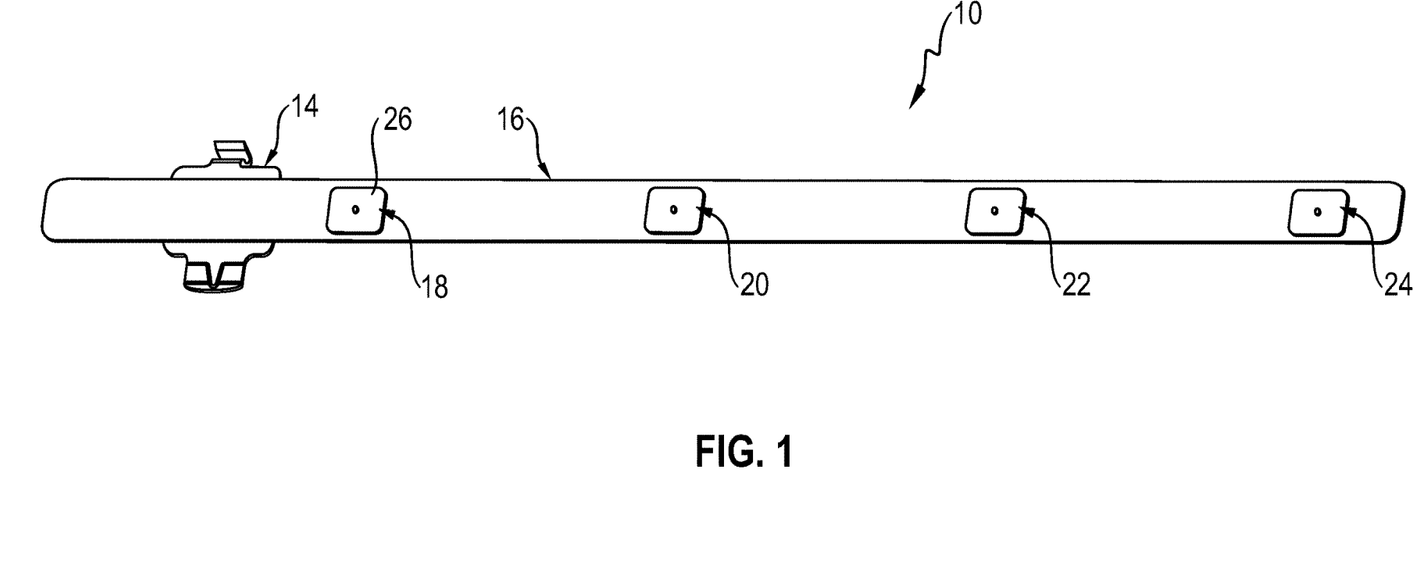
FIG. 1 shows a perspective view of an embodiment of a sensing device in accordance with aspects of the present disclosure.
Figure 2:
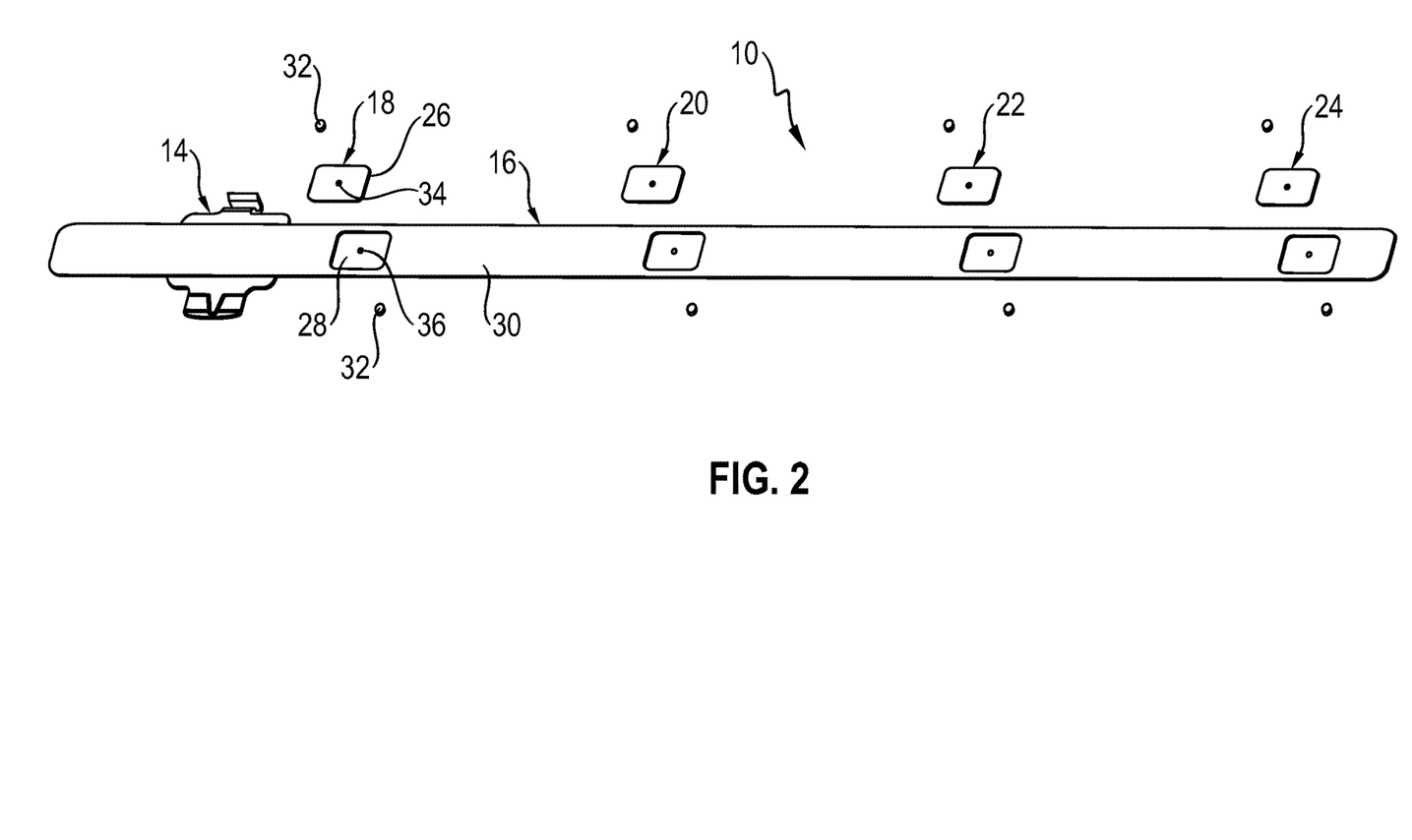
FIG. 2 shows an exploded perspective view of the embodiment of the exemplary sensing device of FIG. 1.
Figure 3:
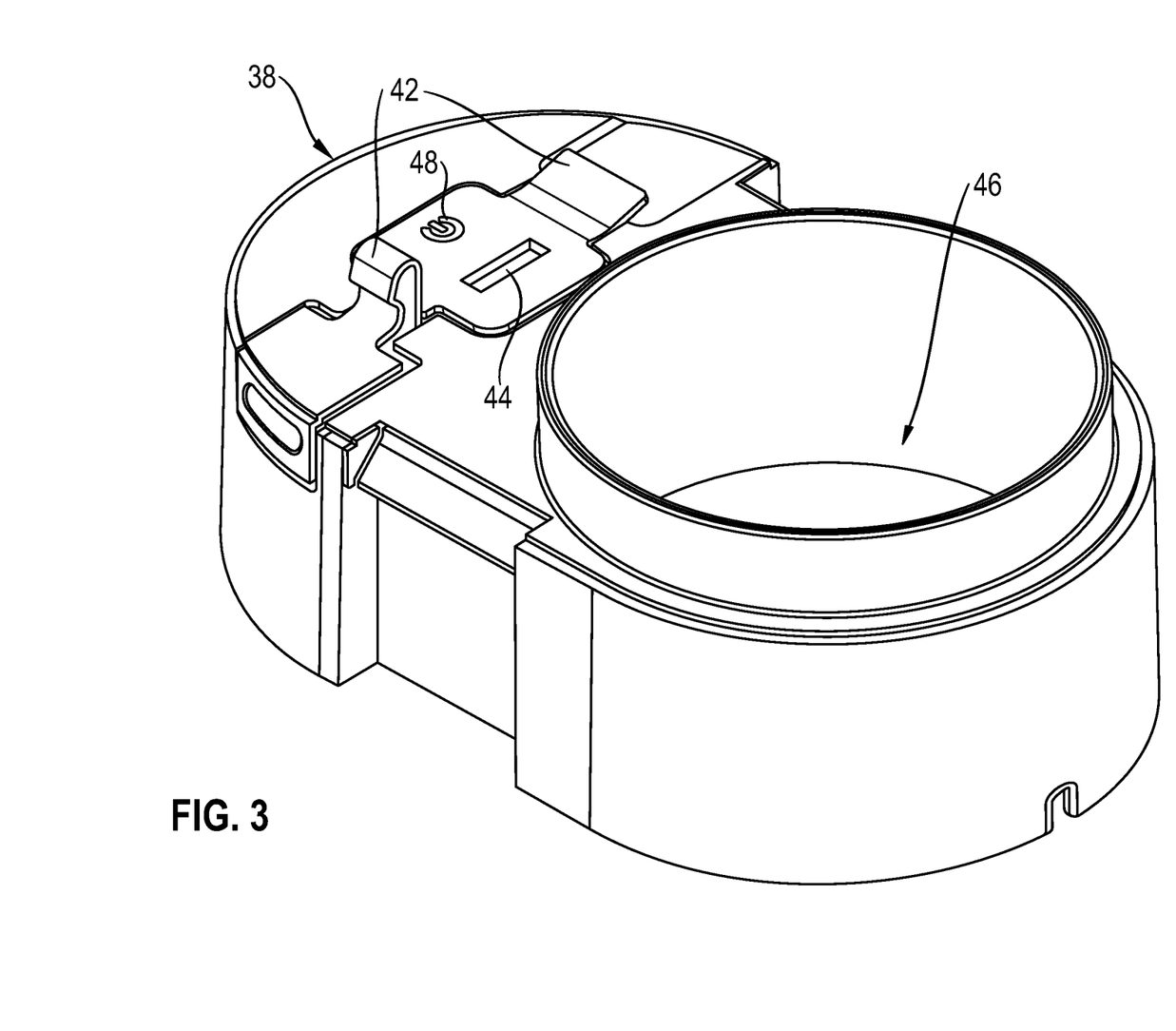
FIG. 3 shows a perspective view of an embodiment of a charging system in accordance with aspects of the present disclosure.
Figure 4A:
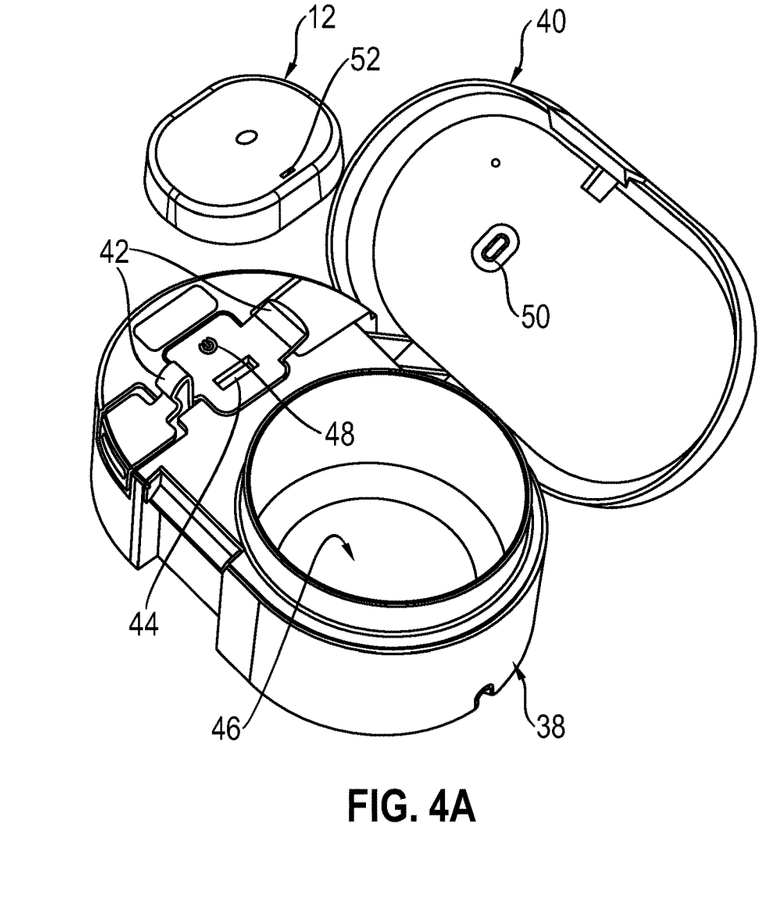
FIG. 4A shows a perspective view of an embodiment of a charging system in accordance with aspects of the present disclosure.
Figure 4B:
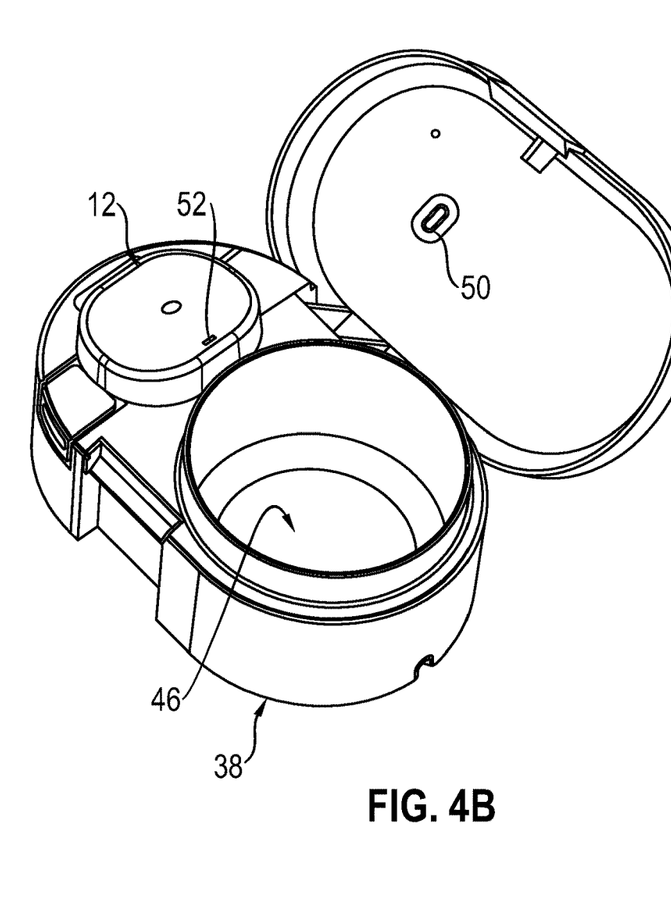
FIG. 4B shows a perspective view of an embodiment of a charging system in accordance with aspects of the present disclosure.

FIGS. 1 and 2 show embodiments of a sensing device for sensing moisture in an absorbent article (such as a baby or an adult diaper) in accordance with aspects of the present disclosure. FIGS. 3, 4A, and 4B show embodiments of a charging system in accordance with the present disclosure. The respective sensing device(s) and the charging system(s) may form a combination of a sensing device and a charging system, the combination being in accordance with the present disclosure.

FIGS. 1 and 2 show views of an embodiment of a sensing device in the form of a sensor strip 10. Further, the corresponding sensing system not only includes the sensing strip 10 but also further includes a transmitter 12 as shown in FIGS. 4A and 4B. The sensing system also includes a first attachment member 14 (FIGS. 1 and 2) for attaching the transmitter 12 to the sensor strip 10.

The sensor strip 10 may include a substrate 16 and one or more sensors 18, 20, 22, and 24 on or in the substrate 16. Although four sensors are depicted on the substrate 16, any suitable number of sensors may be included on the substrate 16, and the sensors may be arranged at any suitable position(s) on the substrate 16.

By way of example, the sensor 18 will now be described in greater detail. It should be understood that sensors 20, 22, and 24 may be similar to, or even identical to, the sensor 18 in accordance with one or more aspects of the present disclosure.

At least a portion of sensor 18 may protrude outwardly away from a surface of the substrate 16. During use, the sensor strip 10 may be applied to an absorbent article so that the surface of the substrate 16 faces an exterior surface of the absorbent article. When the sensor strip 10 is applied to the exterior surface of the absorbent article, the protruding portion of sensor 18 may be in close proximity to the exterior surface of the absorbent article so that sensor 18 may press against the exterior surface of the absorbent article. One or more electrodes (not shown) may be provided in or on sensor 18 for sensing one or more characteristics of the absorbent article, and it is contemplated that the electrodes may be positioned within the protruding portion of the sensor 18, for example at an exposed end face 26 of the sensor 18, to ensure contact, or at least close proximity, between the electrodes and the exterior surface of the absorbent article once the sensor strip 10 is applied to the exterior surface of the absorbent article. Alternatively, the exposed end face 26 may be flush with the surface of the substrate 16. Alternatively, the exposed end face 26 may be recessed from the surface of the substrate 16.

According to an embodiment, the sensor 18 may be made by depositing or embedding one or more conductive elastomers on to the substrate 16.

The substrate 16 may include, for example, a flex printed circuit board (PCB) 28 (see FIG. 2) covered by or embedded within a jacket or coating 30. One or more portions of the jacket 30 may be removed to expose the flex PCB 28, and/or to create a cavity in which sensor 18 may be secured. The sensor 18 may be made by depositing the conductive elastomer on the flex PCB 28. Alternatively, the sensor 18 may be made by embossing a conductive plate on the flex PCB 28, depositing a conductive foam on the flex PCB 28, or mounting one or more leaf springs on the flex PCB 28 (for example, with a leg or legs of the one or more leaf springs extending outwardly to contact the exterior surface of the absorbent article).

It is further contemplated that jacket 30 may be formed by one or more layers of fastening material, such as one of hook and loop engagement members of a VELCRO connection, for engaging the other of hook and loop engagement members on the exterior surface of the absorbent article. Any suitable fastening elements may be used in addition to, or instead of hook and loop engagement members, e.g., buttons, snaps, clasps, magnets, etc.

Additionally or alternatively, the jacket 30 may be formed by different layers of material. For example, a first portion of the jacket 30 may cover one side of the flex PCB 28, that side being the one with the sensors 18, 20, 22, and 24 mounted thereon. The first portion may be formed by one or more layers of fastening material (e.g., part of a VELCRO connection). A second portion of the jacket 30 may cover the opposite side of the flex PCB 28. The second portion may be formed by a different material, such as, for example, a flexible sheet material having smooth exterior surfaces.

As shown in FIG. 2, the sensor 18 may be fastened to the flex PCB 28 by an attachment element 32. The attachment element 32 may include one or more of rivets (shown in FIG. 2), staples, adhesives (conductive or non-conductive), and epoxy. Apertures 34 and 36 may be provided in the sensor 18 and the flex PCB 28, respectively, to receive the attachment element 32.

The first attachment member 14 may attach the transmitter 12 to sensor strip 10. The first attachment member 14 may include any suitable form of mechanical attachment(s)

including, for example, fasteners, adhesives, releasable snap-fit connection mechanisms, magnets, and/or a latch mechanism.

The transmitter 12 may be brought into contact with the first attachment member 14, and the first attachment member 14 may hold the transmitter 12, or vice versa. The transmitter 12 and the first attachment member 14 and/or the sensor strip 10, may include mating electrical connections (not shown) for passing power and/or data in the form of electrical signals, between the transmitter 12 and the sensors 18, 20, 22, and 24. For example, the transmitter 12 may have one or more conductive pads that may contact one or more conductive pads in the sensor strip 10. The flex PCB 28 may connect the conductive pads in the sensor strip 10 with the sensors 18, 20, 22, and 24.

FIGS. 3, 4A, and 4B show aspects of a charging system for charging a battery (not shown) in the transmitter 12. The battery may power one or more of the components of the sensing system. The charging system may include a base 38 and a cover 40. Aspects of these components are described in greater detail below.

The base 38 may include a second attachment member 42 for attaching the transmitter 12 to the base 38. The second attachment member 42 may be similar to the first attachment member 14, and may include one or more electrical connections (not shown) for mating with the electrical connections on the transmitter 12. The electrical connections on the base 38 may be accessible to the electrical connections of the transmitter 12 via a port or window 44. Once connected, the base 38 may charge the battery in the transmitter 12.

The sensor strip 10 may include a port similar to the port 44. The transmitter 12 may be detached from the sensor strip 10 before the transmitter 12 is attached to the second attachment member 42. The sensor strip 10 may be rolled, coiled, or otherwise manipulated to fit within a cavity 46 of the base 38.

According to some embodiments, the base 38 may include a first light source 48. The first light source 48 may emit light whenever the charging system is connected to power, for indicating that the charging system is capable of charging the battery in transmitter 12. The first light source 48 may include, for example, a light-emitting diode (LED). Light from the first light source 48 may be visible when the cover 40 is in an open state (FIGS. 4A and 4B). Light from the first light source 48 also may be visible when the cover 40 swings from the open state to a closed state (in which the cover 40 covers base 38), via an opening or window 50 in the cover 40.

According to one aspect, when a component of the sensing system, such as the transmitter 12, is connected to the base 38, the attached component may cover the first light source 48. Light from the first light source 48 may no longer be visible via the opening 50 in the cover 40 when the first light source 48 is obscured by the attached component.

The attached component, such as the transmitter 12, may include a second light source 52 that may emit light. The light from the second light source 52 may have a different color than the light from the first light source 48, providing users with visual confirmation of whether the charging system is in use, even while the cover 40 is closed, based on the color of light being emitted via the opening 50. It is contemplated that the second light source 52 may be aligned with opening 50 when the cover 40 is in the closed state.

The second light source 52 may indicate the charging status of the battery of the transmitter 12. For example, the second light source 52 may emit light of a first color during charging of the battery, and may emit light of a second color, different than the first color, when the battery is fully charged. Additionally or alternatively, the second light source 52 may emit several different colors of light along the visible spectrum as the state of the battery changes, to indicate the charge status of the battery, or may change in brightness. Additionally or alternatively, the second light source 52 may blink to indicate the charge status of the battery.

The first and second light sources 48 and 52 may provide users with visual confirmation of the connection status of the charging system, and visual confirmation of the charging status of the battery, respectively. The first light source 48 may provide users with visual confirmation of the connection status before the transmitter 12 is clipped in. Once the transmitter 12 is clipped in, it may block light from the first light source 48, while allowing light from the second light source 52 to be seen in the opening 50 of the cover 40 for providing visual confirmation of the charging status of the battery. Displaying a single status light source at a time may prevent confusion about the operational status of the charging system and the charge status of the battery and may indicate when the charging system is in use and when not.

It will be apparent to those skilled in the art that various modifications and variations can be made in the disclosed devices and systems without departing from the scope of the disclosure. Other aspects of the disclosure will be apparent to those skilled in the art from consideration of the specification and practice of the features disclosed herein. It is intended that the specification and examples be considered as illustrative only. Many additional variations and modifications are possible and are understood to fall within the framework of the disclosure.

The invention claimed is:

1. A combination of a sensing device and a charging system, wherein:
   the sensing device comprises a substrate and one or more sensors configured to sense a characteristic of moisture in an absorbent article, the sensing device, including the one or more sensors, being configured to be applied to an outer surface facing away from a wearer of the absorbent article for sensing moisture in the absorbent article through the outer surface, and the sensing device being configured such that a transmitter for transmitting data from the sensing device is removably attached or removably attachable to the sensing device and the one or more sensors, and
   the charging system comprises a charger configured to charge a transmitter battery, the charging system being configured such that the transmitter, which is removably attached or removably attachable to the sensing device, is also attachable to the charging device,
   wherein a surface of the substrate faces an exterior surface of the absorbent article and that at least one of the one or more sensors presses against the exterior surface of the absorbent article, and
   wherein the sensing device is further configured to sense one or both of a location and a position of the wearer of the absorbent article.

2. The combination according to claim 1, wherein the sensing device comprises a first attachment member for attaching a transmitter to the sensing device; and/or
   the charging system comprises a second attachment member for attaching a transmitter to the charging system.

3. The combination according to claim 2, wherein the first attachment member comprises at least one of a fastener, a conductive or non-conductive adhesive, a releasable snap-fit connection mechanism, a magnet, a rivet, a staple, epoxy, or a latch mechanism; and/or
    the second attachment member comprises at least one of a fastener, a conductive or nonconductive adhesive, a releasable snap-fit connection mechanism, a magnet, or a latch mechanism.

4. The combination according to claim 1, further comprising a sensing system, wherein the sensing system comprises the sensing device and the transmitter.

5. The combination according to claim 4, wherein the transmitter is removably attached or removably attachable to the first attachment member and attachable to the second attachment member.

6. The combination according to claim 4, wherein the first attachment member and the transmitter comprise mating electrical connections; and/or
    the second attachment member and the transmitter comprise mating electrical connections.

7. The combination according to claim 4, wherein the transmitter is detachable from the first attachment member and/or from the second attachment member.

8. The combination according to claim 1, wherein the sensing device is further configured to sense movements, a location, or a position of the wearer of the absorbent article.

9. The combination according to claim 1, wherein the characteristic of moisture includes at least one of a presence of moisture in the absorbent article or an amount of moisture in the absorbent article.

10. The combination according to claim 2, wherein the charging system further comprises a base, wherein the base comprises the second attachment member for attaching a transmitter to the base.

11. The combination according to claim 10, wherein the base comprises a cavity for accommodating the sensing device.

12. The combination according to claim 1, wherein the charging system further comprising a first light source, the charging system being configured to emit light with the first light source for indicating at least one of whether the charging system is capable of charging a transmitter battery, whether the charging system is connected to power, whether a transmitter is attached, or whether the transmitter is charging.

13. The combination according to claim 12, wherein the charging system further comprises a cover, the cover comprising an opening or window allowing light emitted from the first light source to be visible from outside of the charging system when the cover is closed.

14. The combination according to claim 13, wherein the charging system comprises a second attachment member for attaching a transmitter to the charging system, and wherein the second attachment member and the first light source are positioned such that a transmitter covers the first light source when the transmitter is attached to the second attachment member.

15. The combination according to claim 14, wherein the combination further comprises the transmitter, the transmitter including a second light source, and wherein the opening or window is positioned on the cover such that light emitted from the second light source is visible from outside of the charging system when the transmitter is attached to the second attachment member and the cover is closed.

16. The combination according to claim 15, wherein the transmitter is configured to emit light with the second light source for indicating a charging status of a battery of the transmitter.

17. The combination according to claim 1, wherein the sensing device is configured to electrically connect with the transmitter via one or more electrical connections provided on each of the sensing device and the transmitter.

18. The combination according to claim 17, wherein the charging system is configured to electrically connect with the transmitter via one or more electrical connections provided on the charger that mate with the one or more electrical connections provided on the transmitter.

19. A sensing device comprising a substrate and one or more sensors configured to sense a characteristic of moisture in an absorbent article, the sensing device, including the one or more sensors, being configured to be applied to an outer surface facing away from a wearer of the absorbent article for sensing moisture in the absorbent article through the outer surface, and the sensing device being configured such that a transmitter for transmitting data from the sensing device is removably attached or removably attachable to the sensing device and the one or more sensors,
    wherein a surface of the substrate faces an exterior surface of the absorbent article and that at least one of the one or more sensors presses against the exterior surface of the absorbent article, and
    wherein the sensing device is further configured to sense one or both of a location and a position of the wearer of the absorbent article.

20. The sensing device according to claim 19, wherein the substrate and one or more sensors form a sensor strip.

21. The sensing device according to claim 20, wherein the sensing device consists of the sensor strip and a first attachment member.

22. The sensing device according to claim 19, wherein said substrate comprises a flex printed circuit board (PCB) covered within a jacket or a coating.

23. The sensing device according to claim 19, wherein at least one of the one or more sensors protrudes outwardly away from a surface of the substrate.

24. The sensing device according to claim 23, wherein the at least one sensor comprises an electrode provided in a protruding portion of said sensor.

25. The sensing device according to claim 19, wherein at least one of the one or more sensors is at least partially formed by one or more conductive elastomers embedded in or deposited on the substrate.

26. The sensing device according to claim 19, wherein the sensing device is configured to be applied to an absorbent article so that a surface of the substrate faces an exterior surface of the absorbent article and that at least one of the one or more sensors presses against the exterior surface of the absorbent article.

27. A charging system comprising a charger configured to charge a transmitter battery of a transmitter for transmitting data from a sensing device configured to be applied to an outer surface facing away from a wearer of an absorbent article for sensing moisture in the absorbent article through the outer surface, wherein the charging system is configured to receive the transmitter that is detachably attachable to the sensing device, and the one or more sensors, and the charging system, the charging system comprising a first light source, the charging system further being configured to emit light with the first light source for indicating at least one of whether the charging system is capable of charging a transmitter battery, whether the charging system is connected to power, whether a transmitter is attached, or whether the transmitter is charging, wherein the sensing device is configured to electrically connect with the transmitter via one or more electrical connections provided on each of the sensing device and the transmitter, and wherein the charging system is configured to electrically connect with the transmitter via one or more electrical connections provided on the charger that mate with the one or more electrical connections provided on the transmitter, wherein the sensing device comprises a substrate and one or more sensors configured to sense a characteristic of moisture in the absorbent article, wherein a surface of the substrate faces an exterior surface of the absorbent article and that at least one of the one or more sensors presses against the exterior surface of the absorbent article, and wherein the sensing device is further configured to sense one or both of a location and a position of the wearer of the absorbent article.

* * * * *